United States Patent
Chen et al.

(10) Patent No.: US 7,983,128 B2
(45) Date of Patent: Jul. 19, 2011

(54) APPARATUS AND METHOD FOR DETECTING DEFECT OF OPTICAL DISC

(75) Inventors: Ching-Chuan Chen, Taichung (TW); Yi-Chun Lin, Taichung (TW)

(73) Assignee: Sunplus Technology Co., Ltd, Hsinchu (TW)

( * ) Notice: Subject to any disclaimer, the term of this patent is extended or adjusted under 35 U.S.C. 154(b) by 522 days.

(21) Appl. No.: 12/116,551

(22) Filed: May 7, 2008

(65) Prior Publication Data

US 2008/0279071 A1    Nov. 13, 2008

(30) Foreign Application Priority Data

May 9, 2007    (TW) .............................. 96116540 A (51) Int. Cl.
*G11B 7/00* (2006.01)
(52) U.S. Cl. ................ 369/53.17; 369/53.15; 369/44.32; 369/44.33
(58) Field of Classification Search ................ 369/53.15, 369/53.16, 53.17, 44.32, 44.33, 47.14
See application file for complete search history.

(56) References Cited

U.S. PATENT DOCUMENTS

| | | | |
|---|---|---|---|
| 5,818,804 A | 10/1998 | Obata et al. | |
| 6,683,830 B2 | 1/2004 | Eom | |
| 7,057,991 B2 | 6/2006 | Park et al. | |
| 7,791,993 B2* | 9/2010 | Kikugawa et al. | 369/47.14 |
| 2001/0055247 A1* | 12/2001 | Tateishi et al. | 369/44.32 |
| 2001/0055524 A1 | 12/2001 | Jackson et al. | |
| 2003/0053381 A1* | 3/2003 | Takahashi et al. | 369/30.24 |
| 2004/0228234 A1* | 11/2004 | Tateishi et al. | 369/44.29 |
| 2005/0265170 A1 | 12/2005 | Pan et al. | |
| 2006/0013095 A1 | 1/2006 | Liu et al. | |
| 2006/0092791 A1* | 5/2006 | Mashimo et al. | 369/47.48 |
| 2006/0215509 A1* | 9/2006 | Yun et al. | 369/47.1 |
| 2009/0196130 A1* | 8/2009 | Yanagawa et al. | 369/30.22 |

FOREIGN PATENT DOCUMENTS

| | | |
|---|---|---|
| TW | 200634739 | 10/2006 |
| TW | 200638413 | 11/2006 |
| WO | 2007029567 | 3/2007 |

* cited by examiner

*Primary Examiner* — Adam R Giesy
(74) *Attorney, Agent, or Firm* — WPAT, PC; Justin King (57) ABSTRACT

A method for detecting a defect of an optical disc includes steps of: confirming an optical pickup head being accessing data in a track on state; determining a defective region of the optical disc according to a peak-to-peak value of a wobble signal; and, maintaining the optical pickup head being unchanged when the defective region is detected.

8 Claims, 9 Drawing Sheets

APPARATUS AND METHOD FOR DETECTING DEFECT OF OPTICAL DISC

FIELD OF THE INVENTION

The invention relates to an apparatus and a method for detecting defects in an optical disc, in particular to an apparatus and a method for detecting defects in an optical disc by using a wobble signal.

BACKGROUND OF THE INVENTION

Figure 1:
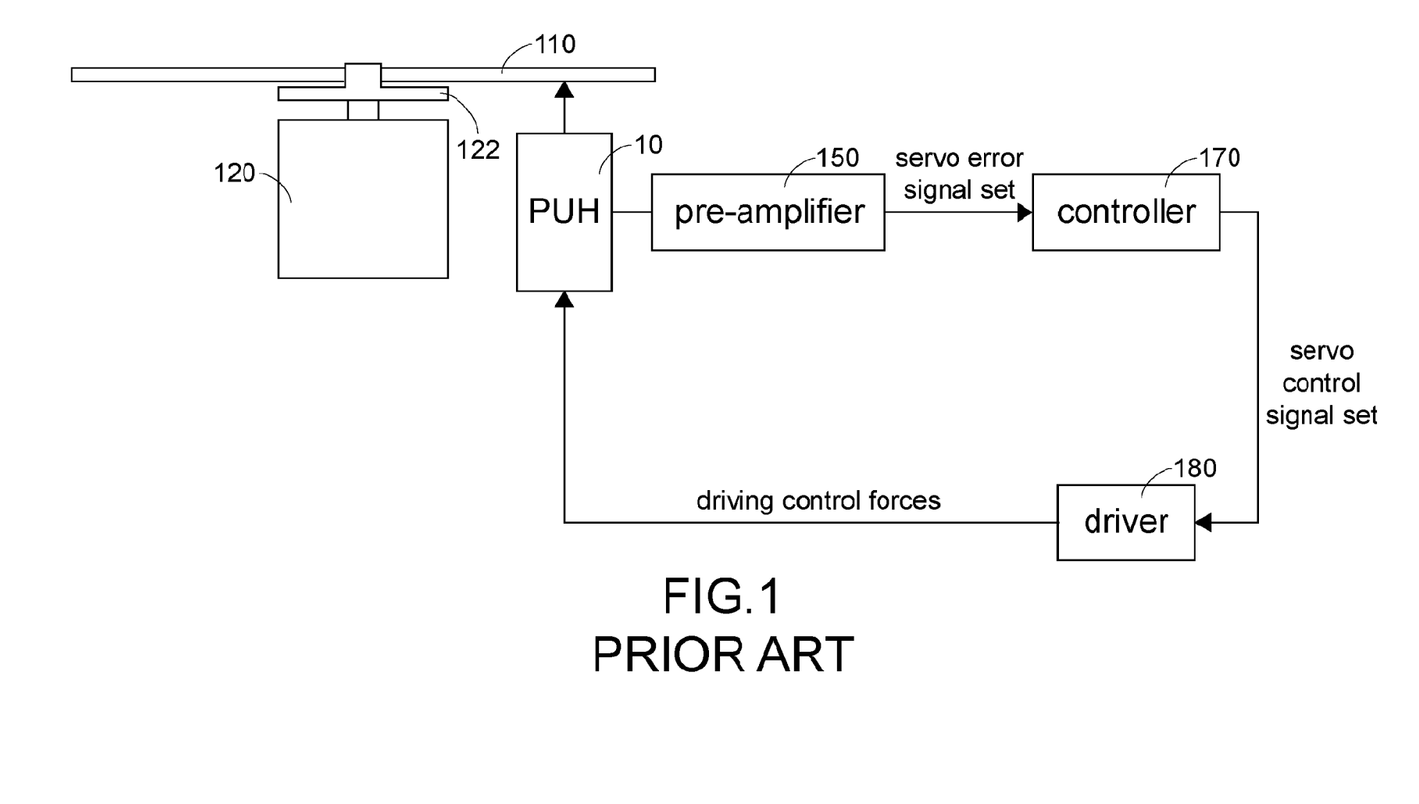
FIG. 1 illustrates a servo control system of an optical disc drive.

Please refer to FIG. 1, which illustrates a servo control system of an optical disc drive, in which, the optical disc drive comprises an optical pickup head ("PUH") 10, and a disc 110 including a center hole can be fixed on a turn table 122 and be rotated by a spindle motor 120. The driver 180 can generate driving control forces to enable the optical pickup head 10 to produce a radial-direction movement and a focusing-direction movement.

The weak signals that are generated when optical pickup head 10 is accessing disc 110 are received and processed by pre-amplifier 150 and a servo error signal set is outputted by the pre-amplifier 150. The servo error signal set, for instance, includes a radio-frequency (RF) signal, a sub-beam added signal (SBAD) signal, a wobble signal, a tracking error signal (TE) and a focusing error signal (FE), etc. The servo error signal set is input into a controller 170 for process and application.

According to the servo error signal set, the controller 170 can output a servo control signal set to the driver 180. The servo control signal set includes at least a tracking control signal and a focusing control signal; and a driver 180 comprises at a least tracking coil and a focusing coil. When the tracking control signal is input into the tracking coil, a driving control force is generated to enable the optical pickup head 10 to produce a radial-direction movement. Also, when the focusing control signal is input into the focusing coil, another driving control force is generated to enable the optical pickup head 10 to produce a focusing-direction movement. Therefore, under normal operation, the driving control forces can maintain the optical pickup head 10 on appropriate focusing position and move along the disc track.

However, because imperfections in the disc manufacture process or scrape of disc both result in defects of disc, when optical pickup head 10 meets a defective region as it reads the disc, the servo error signal set output from the pre-amplifier 150 will be abnormal, which leads to the output of abnormal servo control signal set by controller 170. This further causes inability of driver 180 to control optical pickup head 10 correctly and optical disc drive servo control system becomes unstable. When the servo control system is unstable, the optical pickup head 10 may produce either focusing failure or off track which leads to the disc not able to be accessed or access error. Furthermore, the controller 170 comprises an auto gain controller (AGC) in order to adjust dynamically gain of the wobble signal. When optical pickup head 10 meets a defective region as it reads a disc, auto gain controller will continuously increase the gain of wobble signal because the wobble signal is too small.

The US publication number 20050265170 provides a method for determining defective blocks of optical disc. The method compares sub-beam added signal (SBAD) and its low-pass filtered signal ($SBAD_{lowpass}$). When the absolute value of the difference between the two signals is greater than a threshold, the related region will be defined as a defective region. Please refer to FIG. 2, which illustrates the signals of conventional optical disc drive detecting defective region of disc. As the optical pickup head emits a beam along the track for accessing data, if the track appears a bright defect, like a region with too strong reflecting rate, sub-beam added signal (SBAD) will rise sharply and its low-pass filtered signal ($SBAD_{lowpass}$) will rise slowly. When the absolute value of the difference between the two signals exceeds a value M, a defective signal (DEFECT) generated by the controller 170 will change to a first level (such as high level). When the absolute value of the difference between the two signals becomes lower than the value M, defective signal (DEFECT) will return to a second level (such as low level).

Figure 2:
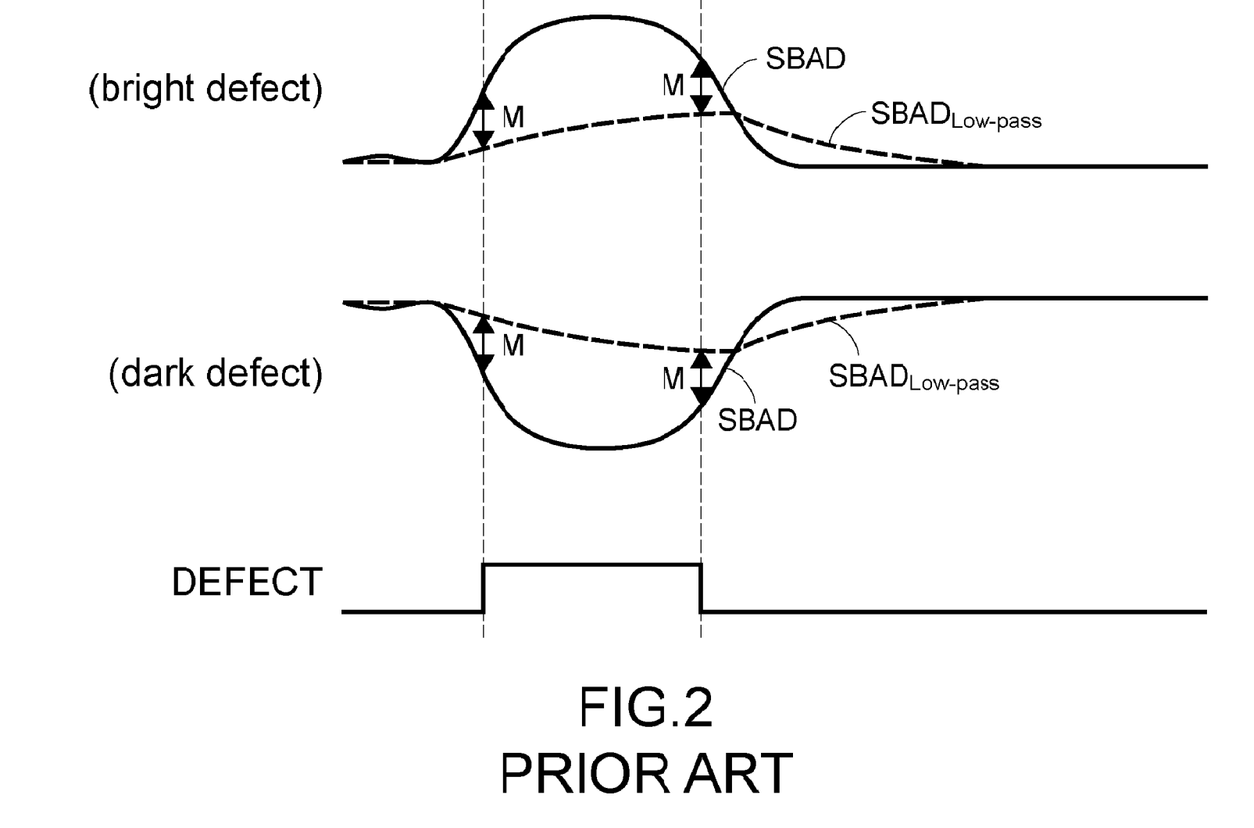
FIG. 2 illustrates the signals of conventional optical disc drive detecting defective region of disc.

By the same logic, if the track appears a dark defect, for instance the scrape region, sub-beam added signal (SBAD) will drop sharply and its low-pass filtered signal ($SBAD_{lowpass}$) will drop slowly. When the absolute value of the difference between the two signals exceeds a value M, the defective signal (DEFECT) generated by the controller 170 will go to the first level. When the absolute value of the difference between the two signals becomes lower than the value M, the defective signal (DEFECT) will return to the second level. By using the defective signal (DEFECT), the driver 180 can adjust driving control forces in time for optical drive to avoid focusing failure or off track.

Figure 3:
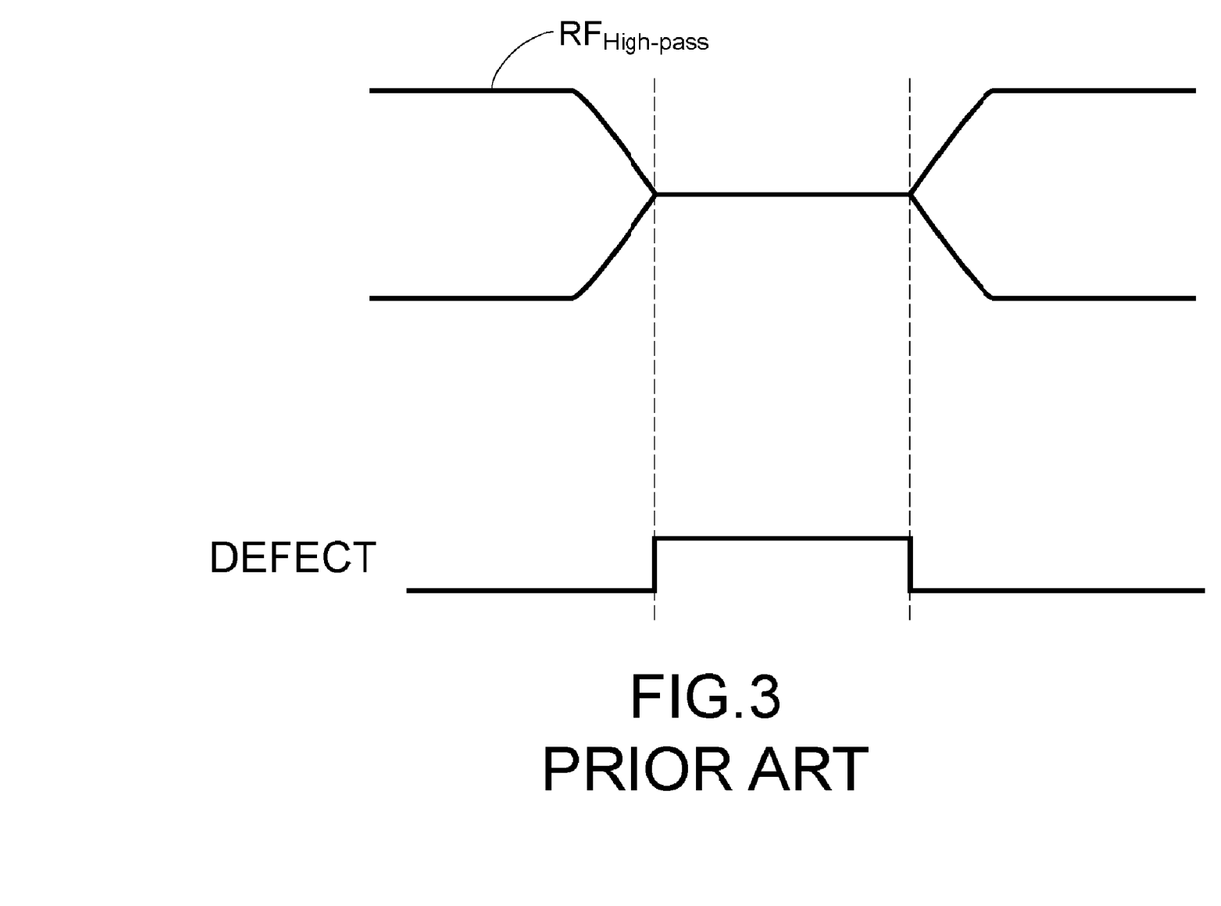
FIG. 3 illustrates signal diagram of conventional optical disc drive detecting defective region.

Further, radio frequency (RF) signal can also be used to determine the defective region of a disc. Please refer to FIG. 3, which illustrates signal diagram of conventional optical disc drive detecting defective region. The method diagnoses the high-pass filtered radio frequency signal ($RF_{High\_Pass}$). As optical pickup head emits a beam along the track to access data, if the beam meets a defective region, the high-pass filtered radio frequency signal ($RF_{High\_Pass}$) will suddenly drop, pre-amplifier 150 will then change the defective signal (DEFECT) to a first level (e.g. high level) and not return to a second level until $RF_{High\_Pass}$ returns to normality. By using the defective signal, driver 180 can adjust driving control forces in time for optical drive to avoid focusing failure or track off.

The aforementioned methods determine a defective region by using energy summation of reflecting laser beam to generate RF signal or SBAD signal. However, as track shape becomes defective during manufacture process, energy summation of reflecting laser beam does not vary obviously. It results in drive cannot detect disc shape changed and cannot control optical pickup head. It also leads to focusing fail or track off so that data stored in the disc cannot be accessed.

SUMMARY OF THE INVENTION

Therefore, the present invention provides an apparatus for detecting a defect of an optical disc, comprising: a spindle motor for rotating the optical disc; an optical pickup head being capable of accessing the optical disk according to driving control forces to enable the optical pickup head to produce a focusing-direction movement and a radial-direction movement; a pre-amplifier connected to the optical pickup head for receiving and processing signals generated by the optical pickup head and to generate a servo error signal set including a wobble signal; a controller connected to the pre-amplifier for processing the servo error signal set to generate a servo control signal set; a driver connected to the controller for generating the driving control forces according to the servo control signal set; and, a track defect detector connected to the pre-amplifier for determining a defective region according to the wobble signal; wherein when the defective region is detected, a defective signal is generated by the track defect detector to the controller for maintaining the servo control signal set.

The present invention further provides a method for detecting a defect of an optical disc, comprising: confirming an optical pickup head being accessing data in a track on state; slicing a wobble signal to form a digital wobble signal; determining a defective region of the optical disc according to the digital wobble signal; and, maintaining the optical pickup head when the defective region is detected.

The present invention further provides a method for detecting a defect of an optical disc, comprising: confirming an optical pickup head being accessing data in a track on state; determining a defective region of the optical disc according to a peak-to-peak value of a wobble signal; and, maintaining the position of optical pickup head being unchanged when the defective region is detected.

BRIEF DESCRIPTION OF THE DRAWINGS

The above contents of the present invention will become more readily apparent to those ordinarily skilled in the art after reviewing the following detailed description and accompanying drawings, in which.

DETAILED DESCRIPTION OF THE PREFERRED EMBODIMENT

Figure 4:
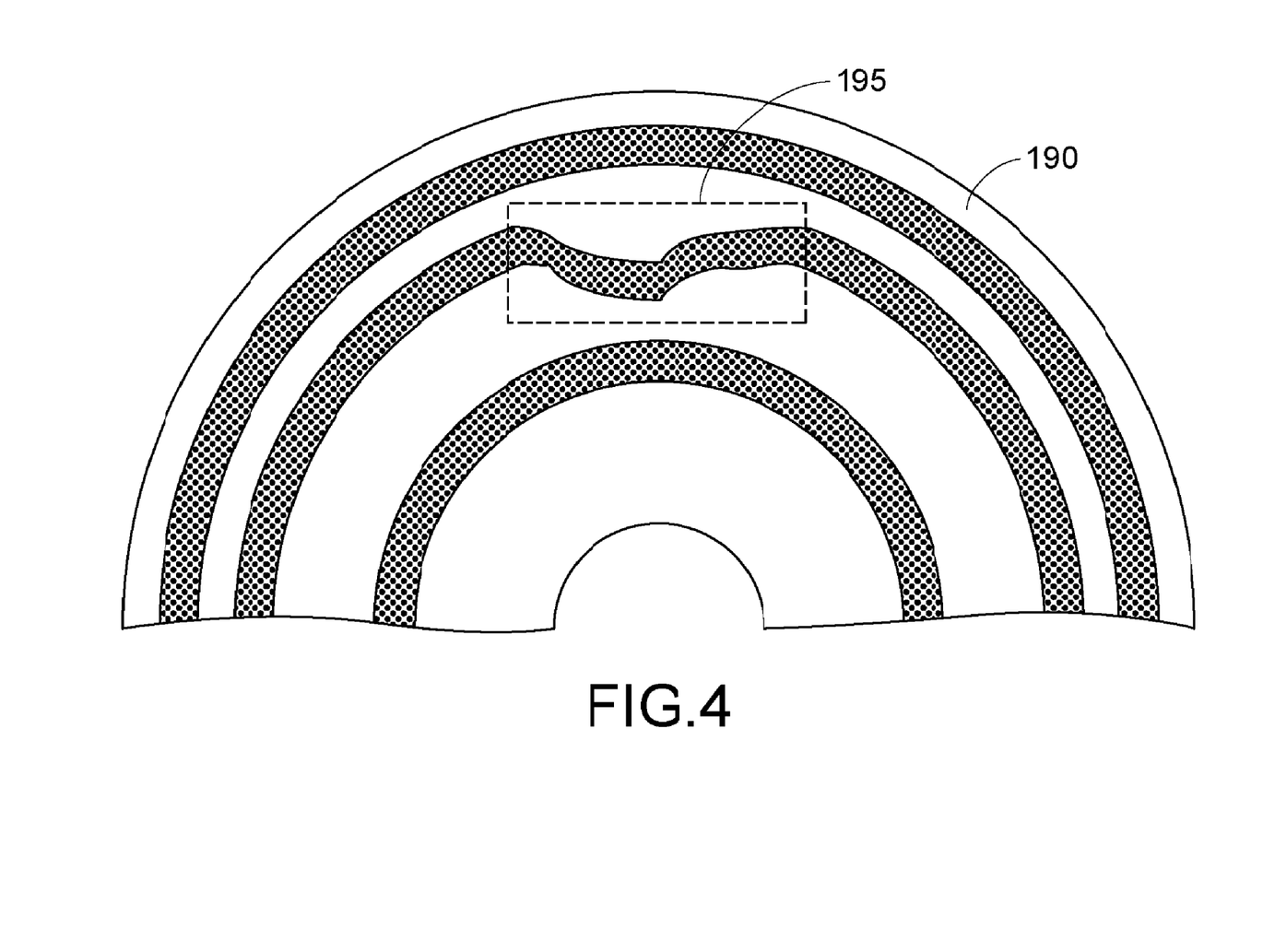
FIG. 4 illustrates a diagram of defective optical disc with shape-changed track.

Please refer to FIG. 4, which illustrates a diagram of defective optical disc with shape-changed track. Ideally, track on the optical disc is a spiral from the inside to the outside. Manufacture defect of discs will form track shape defect 195 on the optical disc 190. As the laser beam emitted from optical pickup head go through track shape defect 195, sub-beam added signal (SBAD) and radio-frequency signal (RF) would not produce an obvious variation. Thus, controller of the conventional optical disc drive cannot detect track shape defect 195 by low-pass filtered signal ($SBAD_{lowpass}$) or high-pass filtered ($RF_{High\_Pass}$).

Therefore, the present invention proposes an apparatus and a method for detecting track shape defects of an optical disc by use of wobble signal. More specifically, the present invention determines whether the region on which optical pickup head is located is a track shape defect region by using a variation of wobble signal. Please refer to FIG. 5, which illustrates a diagram of the presently invented servo control system of optical disc drive, in which the optical disc drive mainly comprises an optical pickup head ("PUH") 510, a disc 515 with a central hole for being fixed on a turn table 522 and be rotated by a spindle motor 520. The driver 580 can generate driving control forces to enable the optical pickup head 510 to produce a radial-direction movement and a focusing-direction movement.

Figure 5:
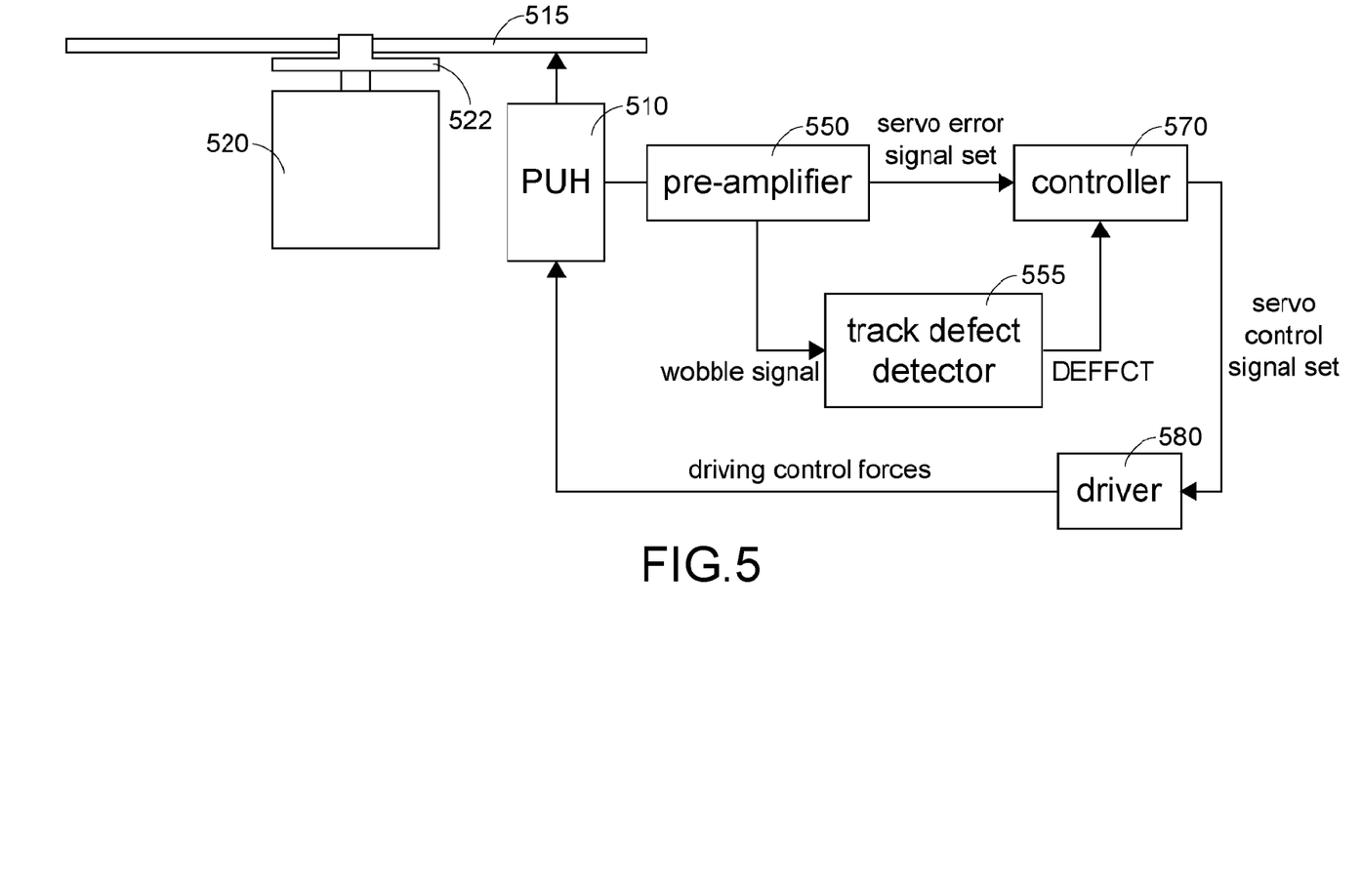
FIG. 5 illustrates a diagram of the presently invented servo control system of optical disc drive.

The weak signals that are generated when optical pickup head 510 is accessing disc 515 are received and processed by pre-amplifier 550 and a servo error signal set is outputted by the pre-amplifier 550. The servo error signal set, for instance, includes a radio-frequency (RF) signal, a sub-beam added signal (SBAD) signal, a wobble signal, a tracking error signal (TE) and a focusing error signal (FE), etc. The servo error signal set is input into a controller 570 for process and application.

According to the servo error signal set, the controller 570 can output a servo control signal set to the driver 580. The servo control signal set includes at least a tracking control signal and a focusing control signal; and a driver 580 comprises at a least tracking coil and a focusing coil. When the tracking control signal is input into the tracking coil, a driving control force is generated to enable the optical pickup head 510 to produce a radial-direction movement. Also, when the focusing control signal is input into the focusing coil, another driving control force is generated to enable the optical pickup head 510 to produce a focusing-direction movement. Therefore, under normal operation, the driving control forces can maintain the optical pickup head 510 on appropriate focusing position and move along the disc track.

According the embodiment of the present invention, a track defect detector 555 is used by the optical disc drive to receive the wobble signal from the pre-amplifier and determine whether the region accessed by the optical pickup head 510 is a track shape defect according to the wobble signal. When track defect detector 555 detects track shape defects, it will output a defective signal (DEFECT) to controller 570. Further, as controller 570 receives a defective signal (DEFECT), it no longer output the servo control signal set to the driver 580 in response to the servo error signal set, but maintains the servo control signal set so that the servo control signal set would not follow the incorrect servo error signal set and result in focus fail or track off thereby leading inability to access or access error of data on to optical disc. Further more, as controller 570 receives a defective signal (DEFECT), it no longer automatically adjust gain of wobble signal but maintains the original one so that optical disc drive does not result in error operation.

Figure 6:
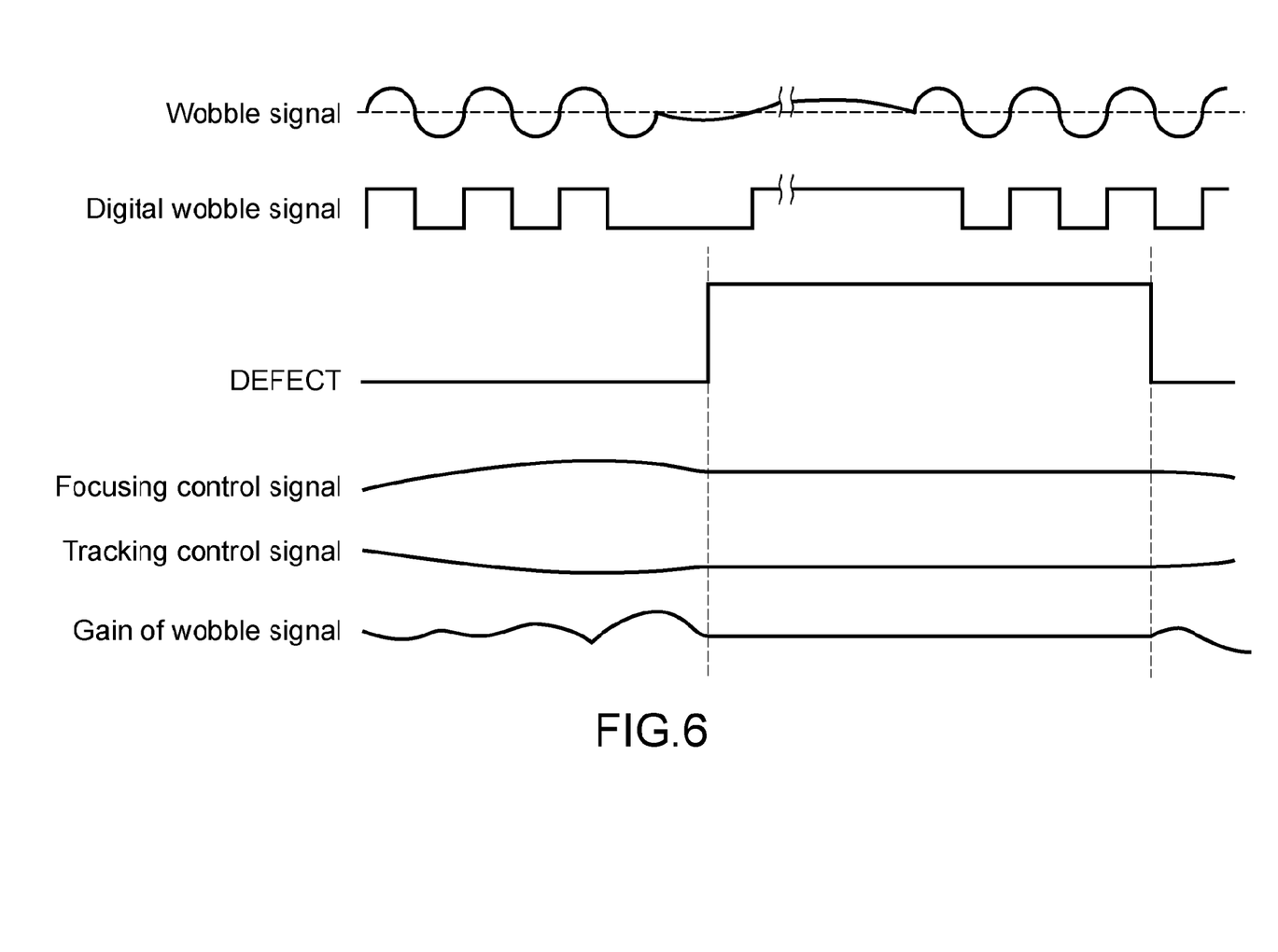
FIG. 6 illustrates the relations among wobble signal, digital wobble signal, defective signal (DEFECT), tracking control signal, focusing control signal and gain of wobble signal.

Please refer to FIG. 6, which illustrates the relations among wobble signal, digital wobble signal, defective signal (DEFECT), tracking control signal, focusing control signal and gain of wobble signal. Because the wobble signal is an analog signal, so a reference level is used to slice the wobble signal to obtain a digital wobble signal. Further, according to the embodiment of the present invention using the wobble signal or such digital wobble signal can determine the track shape defects of a disk.

It can be known from FIG. 6, as optical pickup head accesses data in the track on state, the wobble signal outputted by the pre-amplifier 550 is a sinusoidal wave; on the contrary, when accessing a track shape defect region, the pre-amplifier 550 cannot output the normal sinusoidal wave. Therefore, the track defect detector 555 can determine that the track region being accessed by the optical pickup head is a defective region from the wobble signal or digital wobble signal and output a first level signal (high level) of defective signal (DEFECT). The defective signal (DEFECT) will only return to a second level signal (low level) when wobble signal returns to sinusoidal wave. When controller 570 receives the first level of defective signal, the controller 570 maintains the servo control signal set. That means maintaining the tracking control signal and focusing control signal causes driver 280 to maintain the optical pickup head on its current focus position and track position. When the defective signal (DEFECT) returns to the second level, the controller 570 will produce normal servo control signal set according to the servo error signal set again.

Figure 7:
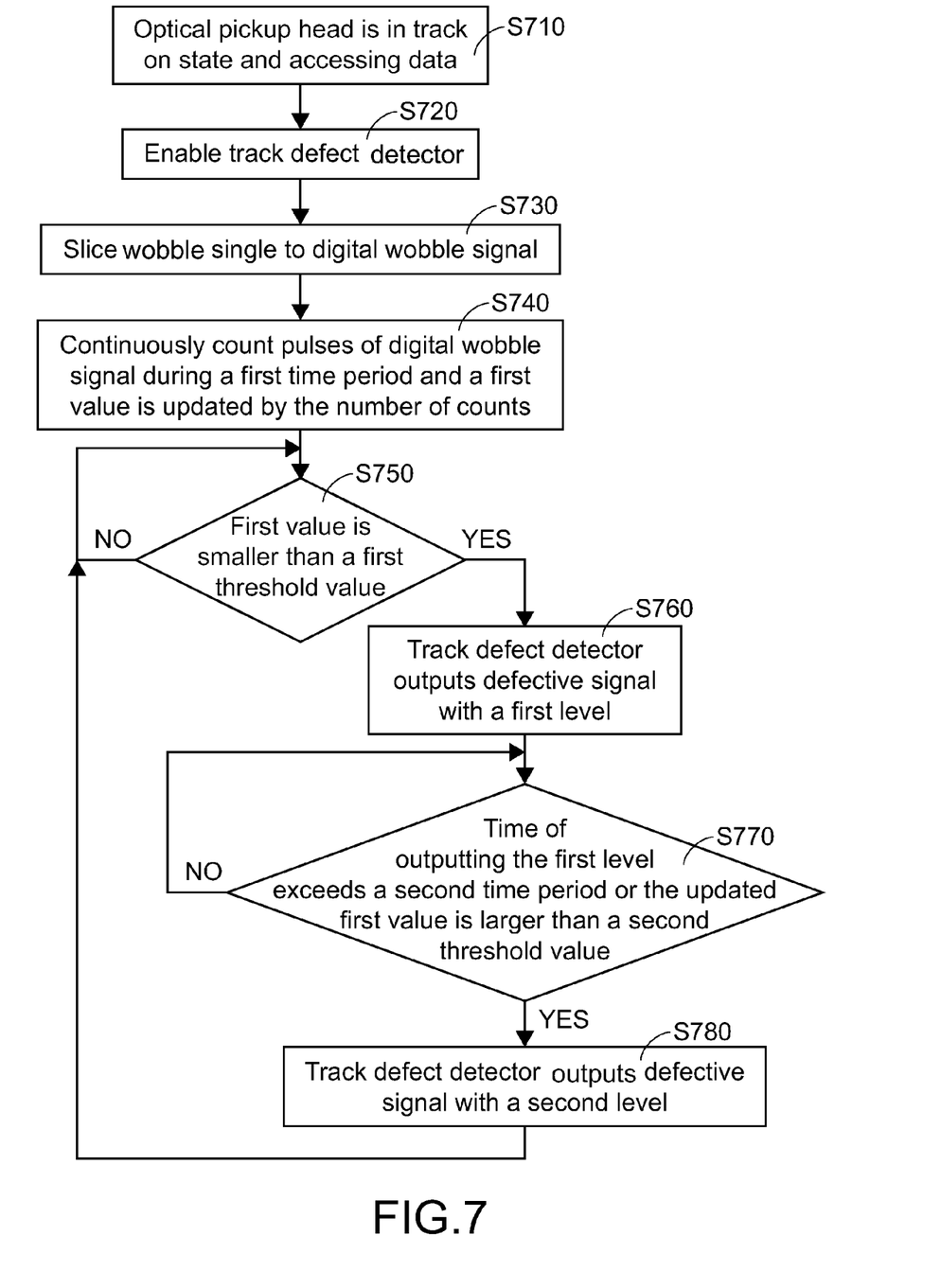
FIG. 7 illustrates the first embodiment of the present invention.

Please refer to FIG. 7, which illustrates the first embodiment of the present invention. First, when the optical disc drive is in normal operation, the optical pickup head is in the track on state and accessing data (S710) and then enable track defect detector (S720). The track defect detector is now able to slice the analog wobble signal into a digital wobble signal (S730). Next, taking a first time period as one time unit continuously to count the pulses of the digital wobble signal, the number of counts becomes a first value, which is repeatedly updated (S740). Next, compare the relationship between the first value and a first threshold value (S750). When the first value is larger than the first threshold value, it means the position of optical pickup head is not in a defective region (normal track). Thus, continue the procedures of comparison (S750). When the first value is smaller than the first threshold value, it means that the position of optical pickup head has entered into the defective region. Track defect detector outputs a defective signal with a first level (high level) (S760). Next, proceed with the step of determining the end of the defective region (S770). When the timing of defective signal with the first level exceeds the second time period or the first value is larger than a second threshold value, then the optical pickup head has left the defective region. Hence, track defect detector outputs the defective signal with a second level (e.g. low level) (S780). On the contrary, when the time of output relating to the first value fails to exceed the second time period and the first value is smaller than the second threshold value, the position accessed by optical pickup head has not left the defective region. Thus, go back to determination step (S770).

According to the embodiment of the presented invention, track defect detector 555 takes the first time period as one unit to continually count the pulse of the digital wobble signal and updates continuously the number into register of control chip. That is to say, the register will renew the latest number of pulse every interval of the first time period. Therefore, when the position accessed by the optical pickup head is not in a defective region, frequency of the wobble signal will be maintained within a specific frequency, and hence frequency of the digital wobble signal will be maintained within a small range of the specific frequency. On the contrary, when the position accessed by optical pickup head is in the defective region, the frequency of wobble signal will decrease and cannot be maintained within a small range of the specific frequency. Consequently, the frequency of digital wobble signal also decreases. By using the aforementioned characteristic, whether the position accessed by the optical pickup head is in the defective region can be determined according to the pulse number of digital wobble signal. In step S750, when the first value exceeds the first threshold value, it means the position accessed by optical pickup head is not in the defective region. On the contrary, when the first value is smaller than the first threshold value, the position being accessed by the optical pickup head has entered into the defective region. Further, in order to prevent detection error, the second threshold value is set higher than the first threshold value, i.e. only when the first value has updated and reached the second threshold value, one can confirm that optical pickup head has left the defective region.

Figure 8:
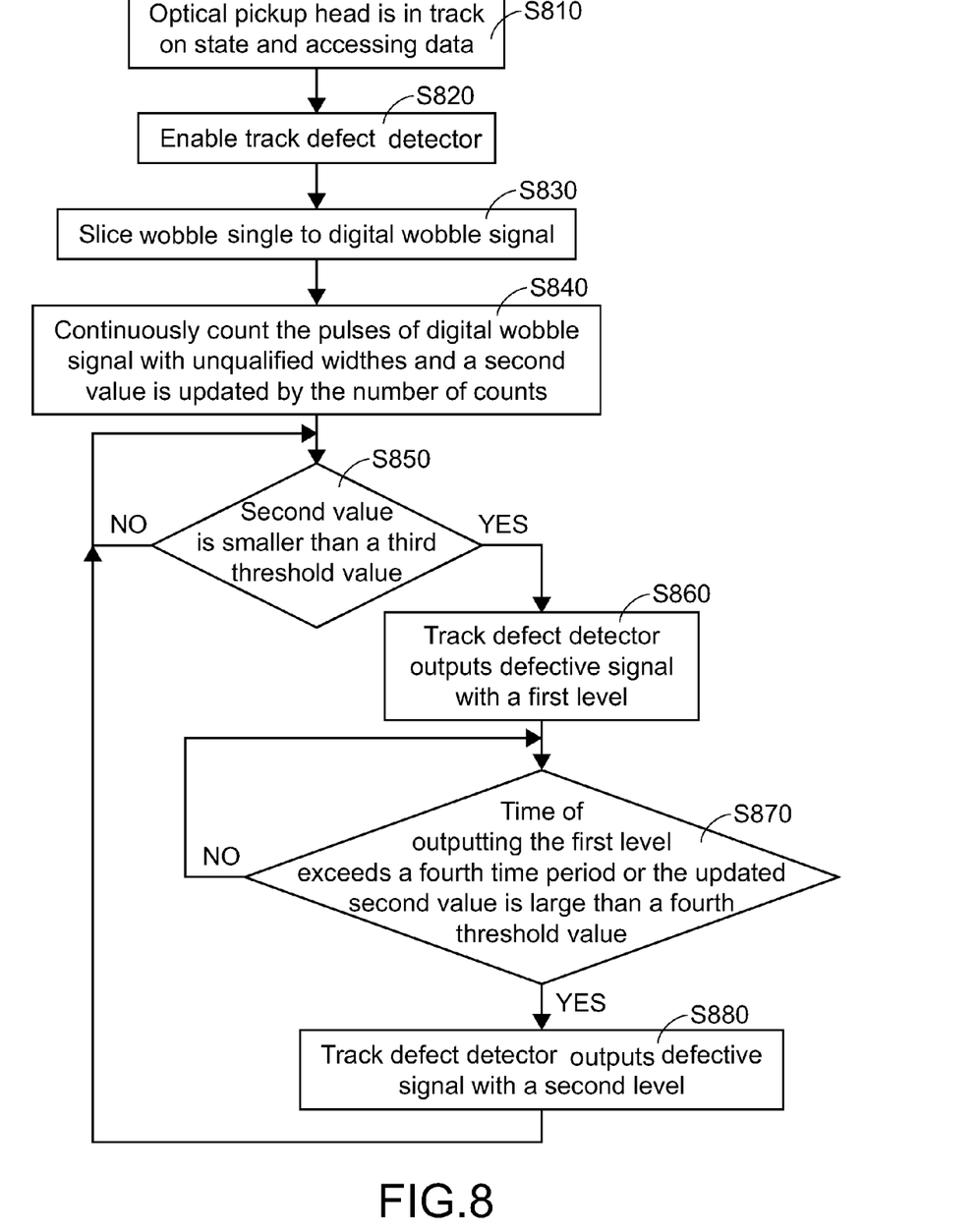
FIG. 8 illustrates the second embodiment of the present invention.

Please refer to FIG. 8, which illustrates the second embodiment of the present invention. First, confirm that optical pickup head is accessing data in the track on state (S810) and then enable track defect detector (S820). The track defect detector is now able to slice the analog wobble signal into a digital wobble signal (S830). Next, taking a third time period as a time unit to count the number of pulses with unqualified widths as the second value in digital wobble signal (S840). Next, compare the relationship between the second value and a third threshold value (S850). When the second value is smaller than the third threshold value, it means the position being accessed by optical pickup head is not in a defective region. Thus, proceed with the comparison step (S850). When the second value exceeds the third threshold value, it means the position accessed by the optical pickup head has entered into a defective region and the track defect detector now outputs a first level (high level) (S860). Next, proceed with the step of determining the end of the defective region (S870). When the time of outputting the first level exceeds the fourth time period or when the second value is smaller than the fourth threshold value, the position being accessed by the optical pickup head can be seen as having left the defective region, hence track defect detector outputs a second level (e.g. low level) (S880). On the contrary, when the time of outputting the first level has not been over the third time period and the second value exceeds the fourth threshold value, the position of the optical pickup head is considered being in the defective region. Hence, go back to the determination procedure (S870).

According to the embodiment of the present invention, track defect detector 555 takes the third time period as one unit to continually count the number of pulses relating to unqualified widths in the digital wobble signal and updates continuously the number into register of control chip. That is to say, the register will renew the latest number of pulses relating to unqualified widths at every interval of the third time period. Therefore, when the position accessed by the optical pickup head is not in the defective region, the frequency and amplitude of the wobble signal will maintain within a small range of a specific frequency and specific amplitude. Thus, the pulse width of sliced digital wobble signal would maintain within a small range of a specific pulse width. Conversely, when the position accessed by the optical pickup head is a defective region, the frequency and amplitude of the wobble signal will decrease. Consequently, the pulse width of digital wobble signal will not be maintained within a small range of a specific pulse width. That is to say, such kind of pulse would be deemed as a pulse with unqualified width. By using the aforementioned characteristics, one can determine whether the position accessed by the optical pickup head is in the defective region according to the number of pulses with unqualified widths. That is to say, in step S850, when the second value is smaller than the third threshold value, the position being accessed by optical pickup head is not in the defective region. Conversely, when the second value exceeds the third threshold value, the position being accessed by the optical pickup head has entered into the defective region. Further, in order to prevent detection error, the second threshold value is set larger than the fourth threshold value, i.e. only when the second values is smaller than the fourth threshold value, one can confirm that optical pickup head has left the defective region.

Figure 9:
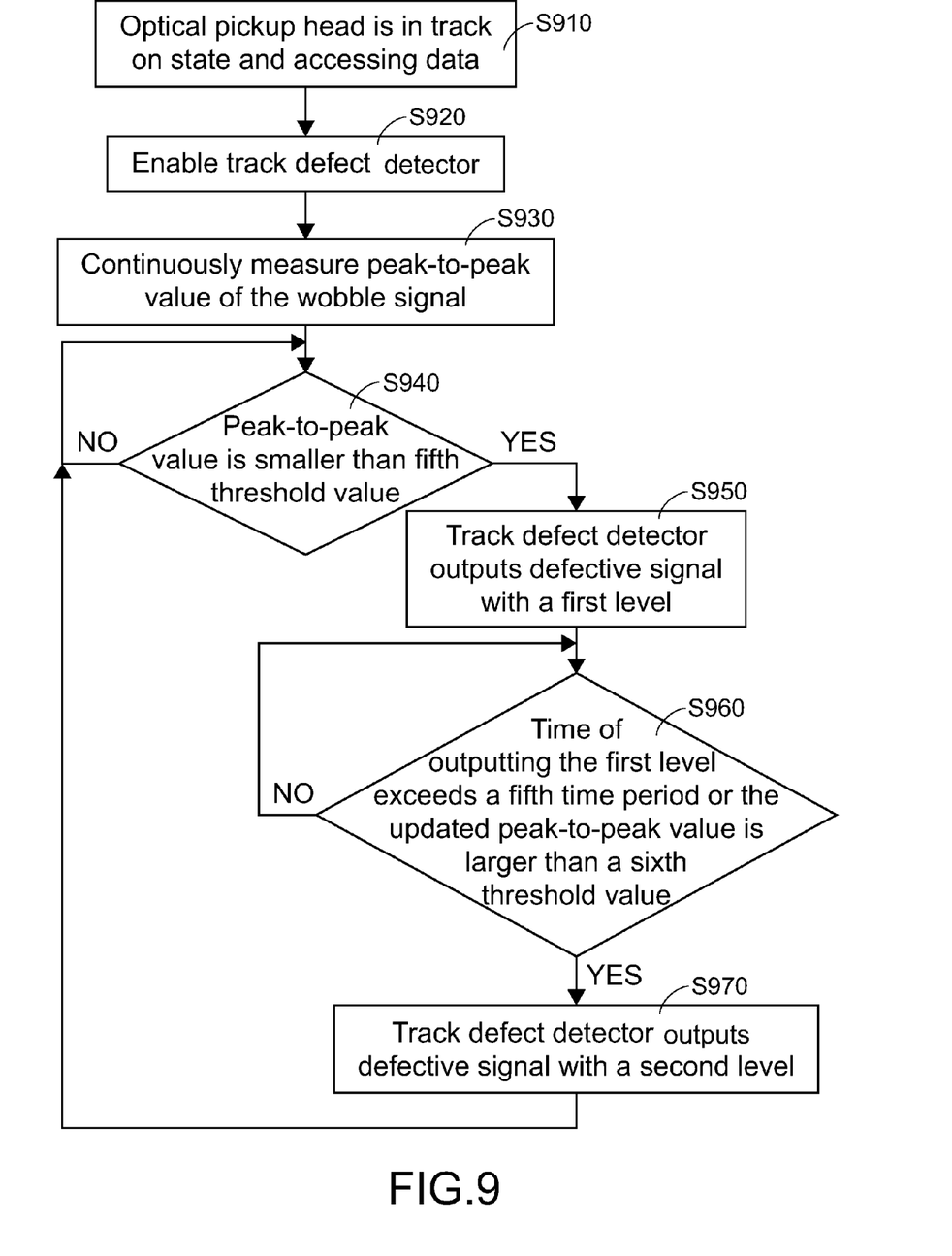
FIG. 9 illustrates the third embodiment of the present invention.

Please refer to FIG. 9, which illustrates the third embodiment of the present invention. First, confirm that optical pickup head is accessing data in the track on state (S910) and track defect detector is enabled (S920). The track defect detector can continuously measure the peak-to-peak value of analog wobble signal (S930). When the peak-to-peak value is larger than the fifth threshold value, it means the position being accessed by the optical pickup head is not in the defective region. Thus, proceed with the comparison step (S940). When the peak-to-peak value is smaller than the fifth threshold value, it means the position accessed by the optical pickup head has entered into the defective region; the track defect detector now outputs a first level (e.g. high level) (S950). Next, proceed with the step of determining the end of the defective region (S960). When the time of outputting the first level exceeds the fifth time period or the peak-to-peak value is larger than the sixth threshold value, the position being accessed by the optical pickup head is deemed to have left the defective region. Hence, track defect detector outputs a second level (e.g. low level) (S970). On the contrary, when the time of outputting the first level does not exceed the fifth time period and the peak-to-peak value is smaller than the sixth threshold value, the position being accessed by the optical pickup head is deemed not to have left the defective region. Thus, we return to determination step (S960).

The embodiment of the present invention utilizes the track defect detector 555 to continuously detect the peak-to-peak value of wobble signal and update continuously the peak-to-peak value into register of control chip. Therefore, when the position being accessed by the optical pickup head is not the defective region, the frequency and amplitude of the wobble signal will be maintained within a small range of a specific frequency and specific amplitude. Conversely, when the position being accessed by the optical pickup head is in the defective region, the frequency and amplitude of the wobble signal will decrease. By using the aforementioned characteristic, one can determine whether the position being accessed by the optical pickup head is in the defective region according to the peak-to-peak value of wobble signal. That is to say, in step S940, when the peak-to-peak value is larger than the fifth threshold value, the position being accessed by the optical pickup head is not in the defective region. Conversely, when the peak-to-peak value is smaller than the fifth threshold value, the position being accessed by the optical pickup head has entered into the defective region. Further, in order to prevent error motion of the track defect detector, the sixth threshold value must be larger than the fifth threshold value, i.e., one must confirm that the peak-to-peak values has reached the sixth threshold value before one can confirm that the position being accessed by the optical pickup head has left the defective region.

As known in the art, there exist many methods of determining track on state of the optical disc drive, the present invention is not limited to the particular method for optical disc drive to determine the track on state. For example, there is a track on signal in optical disc drive control chip. The most common method to determine if optical pickup head is in a track on state is by using the track on signal. Or else, decode the analog wobble signal is to acquire synchronous pattern in the wobble signal. When the wobble signal can be decoded into many synchronous patterns continuously, we can determine that optical pickup head is in the track on state. Likewise, comparison of the frequency relation between digital wobble signal and reference clock in optical disc drive is also a way to determine if optical pickup head is in the track on state.

Therefore, the present invention determines whether the position accessed by an optical pickup head is in the defective region according to wobble signal, which enables the optical disk to detect any track shape defect and control the access of optical pickup head in time. The present invention also effectively solves the problems of error operation, focus fail and track off of optical disc drive.

While the invention has been described in terms of what is presently considered to be the most practical and preferred embodiments, it is to be understood that the invention needs not be limited to the disclosed embodiment. On the contrary, it is intended to cover various modifications and similar arrangements included within the spirit and scope of the appended claims, which are to be accorded with the broadest interpretation so as to encompass all such modifications and similar structures.

What is claimed is:

1. A method for detecting a defect of an optical disc, comprising:
    confirming that an optical pickup head is accessing data in a track on state;
    slicing a wobble signal to form a digital wobble signal;
    continuously counting a first value of pulses of the digital wobble signal during a first time period;
    determining an accessed track as a defective region when the first value is smaller than a first threshold value, otherwise, determining the accessed track as not the defective region;
    maintaining the optical pickup head when the defective region is detected; and
    when the accessed track is set as the defective region, determining the accessed track as an end of the defective track if the first value is larger than a second threshold value or if a time of the optical pickup head in the defective region is larger than a second time period, wherein the second threshold value is larger than the first threshold value.

2. The method according to claim 1, further comprising:
    maintaining a gain of the wobble signal when the accessed track is set as the defective region.

3. A method for detecting a defect of an optical disc, comprising:
    confirming that an optical pickup head is accessing data in a track on state;
    slicing a wobble signal to form a digital wobble signal;
    continuously counting a second value of pulses with unqualified widths of the digital wobble signal during a third time period;
    setting an accessed track as a defective region when the second value is larger than a third threshold value; and
    maintaining the optical pickup head when the defective region is detected.

4. The method according to claim 3, further comprising:
    setting the accessed track as an end of the defective track if the second value is smaller than a fourth threshold value when the accessed track is set as the defective region, wherein the third threshold value is larger than the fourth threshold value.

5. The method according to claim 3, further comprising:
    setting the accessed track as an end of the defective track if a time of the optical pickup head in the defective region is larger than a fourth time period when the accessed track is set as the defective region.

6. The method according to claim 3, further comprising:
    maintaining a gain of the wobble signal when the accessed track is set as the defective region.

7. A method for detecting a defect of an optical disc, comprising:
    confirming that an optical pickup head is accessing data in a track on state;

determining an accessed track as a defective region when a peak-to-peak value of the wobble signal is smaller than a fifth threshold value;

maintaining the position of optical pickup head being unchanged when the defective region is detected when the accessed track is set as the defective region, determining the accessed track as an end of the defective track if the peak-to-peak value of the wobble signal is larger than a sixth threshold value or if a time of setting the defective region is larger than a fifth time period, wherein the sixth threshold value is larger than the fifth threshold value.

8. The method according to claim 7, further comprising:

maintaining a gain of the wobble signal when the accessed track is set as the defective region.

* * * * *